(12) United States Patent
Meyer et al.

(10) Patent No.: US 7,726,313 B2
(45) Date of Patent: Jun. 1, 2010

(54) BREATHING MASK WITH INDIVIDUAL ADAPTATION TO THE SHAPE OF THE FACE

(75) Inventors: Jörg-Uwe Meyer, Ratzeburg (DE); Götz Kullik, Lübeck (DE); Cornelia Schrader, Lübeck (DE); Hans-Ullrich Hansmann, Barnitz (DE)

(73) Assignee: Drägerwerk Aktiengesellschaft, Lübeck (DE)

( * ) Notice: Subject to any disclaimer, the term of this patent is extended or adjusted under 35 U.S.C. 154(b) by 836 days.

(21) Appl. No.: 11/082,427

(22) Filed: Mar. 17, 2005

(65) Prior Publication Data

US 2005/0284478 A1  Dec. 29, 2005

(30) Foreign Application Priority Data

Jun. 23, 2004  (DE) ........................ 10 2004 030 070

(51) Int. Cl.
*A61G 10/00* (2006.01)
*A61M 16/00* (2006.01)

(52) U.S. Cl. ............................. 128/206.11; 128/205.25; 128/205.27; 128/206.18; 128/206.24; 128/206.28; 600/587; 425/385; 264/40.1; 264/320; 264/293

(58) Field of Classification Search ............ 128/205.25, 128/206.24, 205.27, 206.18, 206.28; 600/587; 425/385; 264/40.1, 320, 293
See application file for complete search history.

(56) References Cited

U.S. PATENT DOCUMENTS

| | | | |
|---|---|---|---|
| 3,128,559 A * | 4/1964 | Winter | 33/544 |
| 4,971,051 A | 11/1990 | Toffolon | |
| 5,235,988 A * | 8/1993 | Johnson et al. | 600/587 |
| 5,492,116 A * | 2/1996 | Scarberry et al. | 128/206.24 |
| 6,273,087 B1 * | 8/2001 | Boussignac et al. | 128/204.22 |
| 6,609,516 B2 * | 8/2003 | Hollander et al. | 128/201.17 |
| 6,712,072 B1 * | 3/2004 | Lang | 128/206.27 |
| 6,728,589 B1 * | 4/2004 | Delache et al. | 700/117 |
| 6,923,182 B2 * | 8/2005 | Angadjivand et al. | 128/206.19 |
| 7,008,737 B2 * | 3/2006 | Morales et al. | 430/5 |
| 7,086,400 B2 * | 8/2006 | Shigematsu et al. | 128/205.25 |
| 7,313,829 B1 * | 1/2008 | Serra et al. | 2/2.15 |

FOREIGN PATENT DOCUMENTS

DE  39 35 890  12/1990
EP  0 427 474  5/1991

* cited by examiner

*Primary Examiner*—Patricia M Bianco
*Assistant Examiner*—Nihir Patel
(74) *Attorney, Agent, or Firm*—McGlew and Tuttle, P.C.

(57) ABSTRACT

A sealing frame for a breathing mask is provided that can be adapted to the contours of the face of a mask user in a simple manner. The sealing frame (1), includes a soft plastic material (5) with embedded metal strips (6).

14 Claims, 3 Drawing Sheets

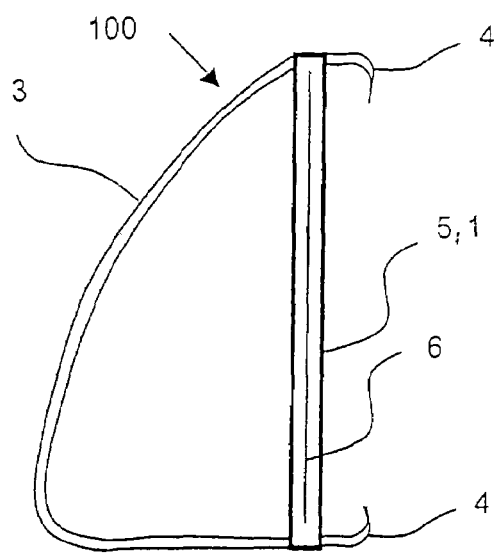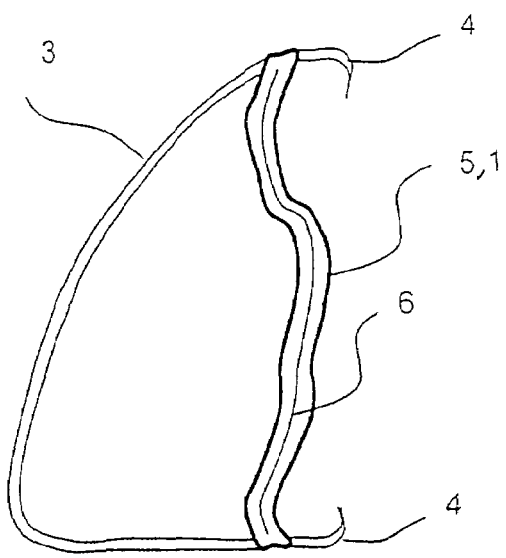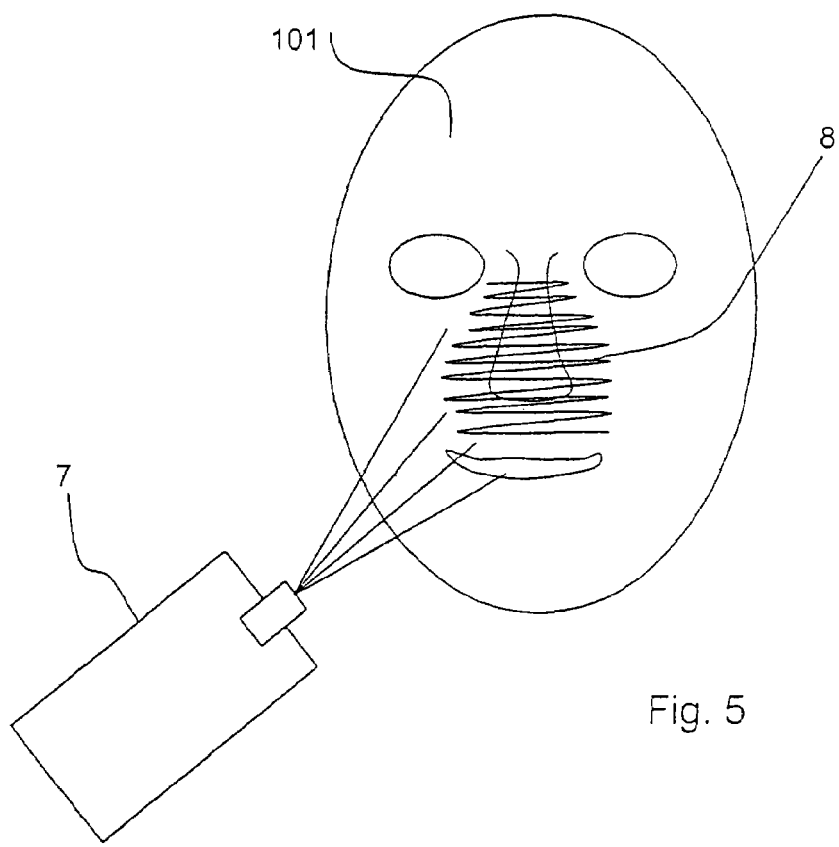

BREATHING MASK WITH INDIVIDUAL ADAPTATION TO THE SHAPE OF THE FACE

CROSS REFERENCE TO RELATED APPLICATIONS

This application claims the benefit of priority under 35 U.S.C. §119 of DE 10 2004 030 070.4 filed Jun. 23, 2004, the entire contents of which are incorporated herein by reference.

FIELD OF THE INVENTION

The present invention pertains to a breathing mask with a plastically deformable sealing frame and to a process for adapting a breathing mask to different face shapes.

BACKGROUND OF THE INVENTION

Persons who need respiratory support or breathing air supply frequently obtain the breathing gas via a breathing mask that is in contact with the face. Such breathing masks are used in the area of occupational safety or in medical applications. The breathing gas is fed in such a case to the user of the mask either breath by breath, or a gas flow is provided, which is discharged continuously via an expiration valve and continuously flushes the interior space of the mask with fresh breathing gas.

The wearing comfort of a breathing mask, which is pressed onto the mask user's face by means of a strap, is determined by a contact line in the form of a sealing frame between the mask body of the breathing mask and the face of the mask user. To adapt the breathing mask to different face shapes, it is known that masks can be offered in different sizes, namely, "small,", "medium" and "large." The individual shape of the face is adapted by a more or less flexible sealing lip. Since the sealing lip must undergo deformation in a relatively large area, it may happen that zones with different pressing pressures will develop on the face.

A sealing frame made of a plastic material for a breathing mask has become known from DE 39 35 890 A1. The sealing frame has a circumferential sealing part, which consists of a special, deformable material. To adapt the sealing part to the shape of the face of the mask user, the material is heated to a relatively low temperature of about 40° C. to 65° C., which does not appear to be too hot to the user of the mask on contact with the skin. The material is selected such that it will harden again at room temperature. During the shaping of the sealing part, the heated and softened material is placed over the face of the mask user and molded corresponding to the contours of the face. The drawback is that a separate heat source must be available.

A breathing mask for positive pressure respiration, in which the sealing frame consists of an inflatable sealing bead, is known from U.S. Pat. No. 4,971,051. A separate hand pump, which must be steadily available for filling in more air, is necessary to inflate the sealing bead.

SUMMARY OF THE INVENTION

The basic object of the present invention is to provide a sealing frame for a breathing mask that can be adapted to the face contours of a mask user in a simple manner. Furthermore, a process for adapting a sealing frame to the shape of the face of a mask user shall be proposed.

The advantage of the present invention is essentially that the sealing frame consists of a soft plastic material, in which plastically deformable metal strips are embedded by injection molding. The sealing frame can thus be adapted to the contours of the face by the mask user himself, without additional auxiliary means being necessary. The rigidity of the sealing frame can be set by selecting the number and the thickness of the metal strips embedded in the plastic material. The user of the mask also has the possibility of making any corrections that may be necessary himself without the need for a complicated apparatus. As an alternative to metal strips, any other plastically deformable material, which can be brought manually to the desired shape, is suitable.

In an advantageous embodiment of the present invention, the sealing frame is made of a polyurethane resin, which can be activated by water. Such materials are known from fixed dressings used in medicine. The sealing frame consists of polyester fabric as a carrier, which is impregnated with polyurethane resin. The sealing frame is then sealed together with the mask body in an air-tight packaging film.

For use, the breathing mask is removed from the packaging film and the sealing edge is wetted with water. The sealing edge is then placed on the face of the mask user and adapted to the face of the mask user. After a short time, when the moisture has escaped, the sealing edge is cured and fully loadable.

The metal strips are advantageously arranged in multiple layers within the sealing frame. The rigidity of the sealing frame can thus be set within a broad range by varying the number of metal strips lying one on top of another or even the manner of coating. It is expedient in this connection to arrange the metal strips or even the metal strips combined in packets uniformly distributed over the circumference.

The suitable materials for the metal strips are aluminum, iron plate or brass. However, also suitable are nonmetallic materials, which can be plastically deformed and have sufficient dimensional stability, so that a corresponding rigidity of the sealing frame in relation to the pressing forces caused by the strap is ensured.

The sealing of the sealing frame on the face of the mask user is advantageously improved by a sealing lip, which is arranged on the side of the sealing frame facing the face. The sealing lip is expediently made directly in one piece with the plastic material of the sealing frame by injection. A degressive spring characteristic of the sealing lip increases the wearing comfort. Such degressive spring characteristic of the sealing lip presents an elastic behavior that is characterized by a degressive spring characteristic in response to stronger forces at greater deflection. In other words, the seal at an edge of the mask body has one or more elastically deformable portion having a spring coefficient that decreases with deflection. This is a seal portion exhibiting a spring force that increases less than linearly with an amount of deflection.

The process described in the present invention comprises:
the detection of the face contours of the mask users with a distance-measuring device,
the selection of a sealing frame made of a plastically deformable material,
the provision of an embossing device for the sealing frame, which has a plurality of stamps for deforming the sealing frame, and
deflecting the stamps in the contact area of the sealing frame on the basis of the distance values determined such that the sealing frame will correspond to a negative mold of the face contours.

The distance measurement may be carried out especially advantageously with a laser distance-measuring unit, which scans the face of the mask user line by line. A three-dimensional view of the surface of the face is first generated. The sealing frame is adapted by means of the embossing device such that it will lie flush on the face. The embossing device has a plurality of electrically operated stamps for this purpose, which are arranged opposite each other and receive corresponding actuating data via the distance-measuring device. The sealing frame is located between the stamps, so that the sealing frame can be deformed by different deflections of individual stamps. The embossing takes place by pressure or also by a combination of pressure and temperature, so that a negative mold of the sealing frame, which corresponds to the surface of the face, can be prepared with the distance data determined for the surface of the face.

An exemplary embodiment of the present invention is shown in the drawings and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is a side view of the undeformed breathing mask;

FIG. 4 shows the breathing mask according to FIG. 3 with deformed sealing edge;

FIG. 5 is a scanning device for the surface of the face of the mask user; and

DESCRIPTION OF THE PREFERRED EMBODIMENTS

Figure 1:
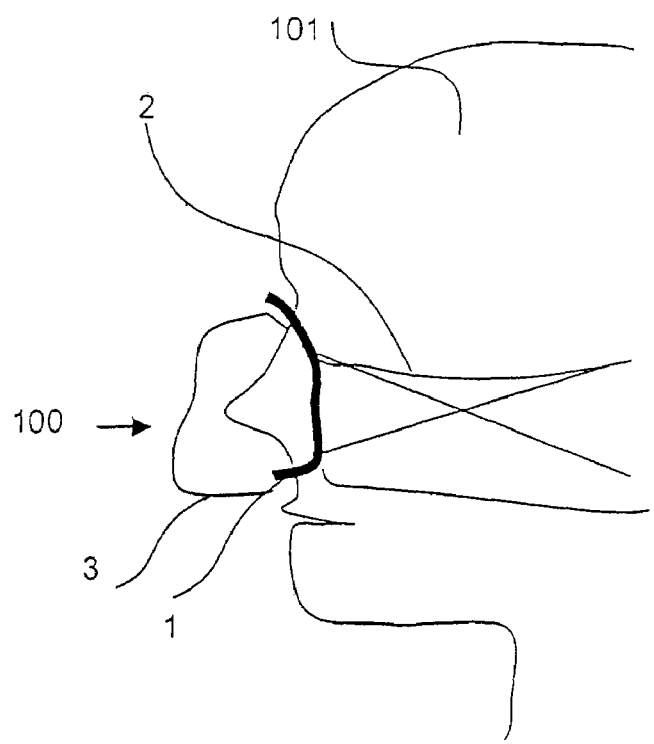
FIG. 1 is a breathing mask placed on the face of a mask user.

Referring to the drawings in particular, FIG. 1 shows a side view of a breathing mask 100 on the face of a mask user 101. The breathing mask 100 comprises a mask body 3, a sealing frame 1, which is in contact with the face, and a strap 2, with which the breathing mask 100 is held on the face.

Figure 2:
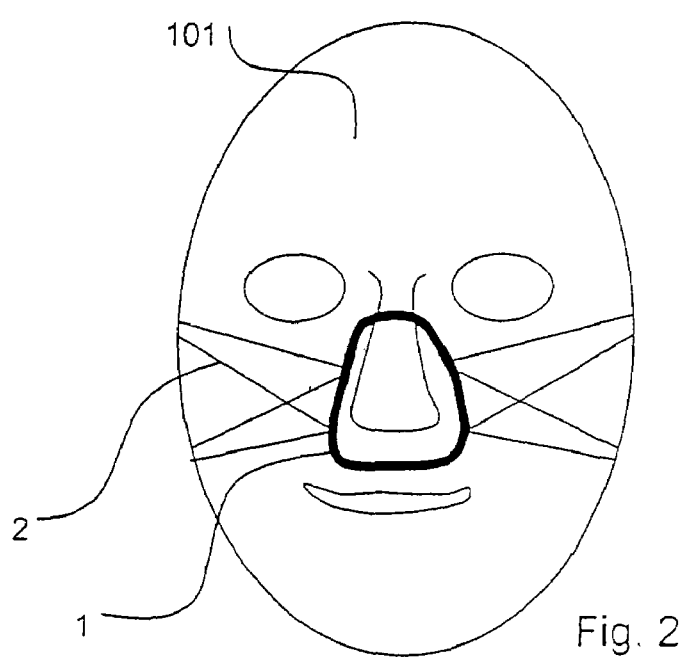
FIG. 2 is a top view of the breathing mask according to FIG. 1.

FIG. 2 shows a top view of the breathing mask according to FIG. 1. Identical components are designated by the same reference numbers as in FIG. 1.

FIG. 3 shows a side view of the breathing mask 100. The sealing frame 1 connected with the mask body 3 consists of a soft plastic material 5 with embedded metal strips 6. A circumferential sealing lip 4 made of a plastic material is arranged on the side of the sealing frame 1 facing the face of the mask user.

The sealing frame soft plastic material 5 may be made of a polyurethane resin, which can be activated by water. Such materials are known from fixed dressings used in medicine. The sealing frame need not include the metal strips and can comprise a polyester fabric as a carrier, which is impregnated with polyurethane resin. The sealing frame is then sealed together with the mask body in an air-tight packaging film. For use, the breathing mask is removed from the packaging film and the sealing edge is wetted with water. The sealing edge is then placed on the face of the mask user and adapted to the face of the mask user. After a short time, when the moisture has escaped, the sealing edge is cured and fully loadable.

FIG. 4 shows the sealing frame 1 adapted to the contours of the face. The metal strips 6 are plastically deformed here and are brought in line with the height contour of the face.

FIG. 5 shows a laser type distance-measuring unit 7, which scans the face of the mask user 101 line by line 8.

Figure 6:
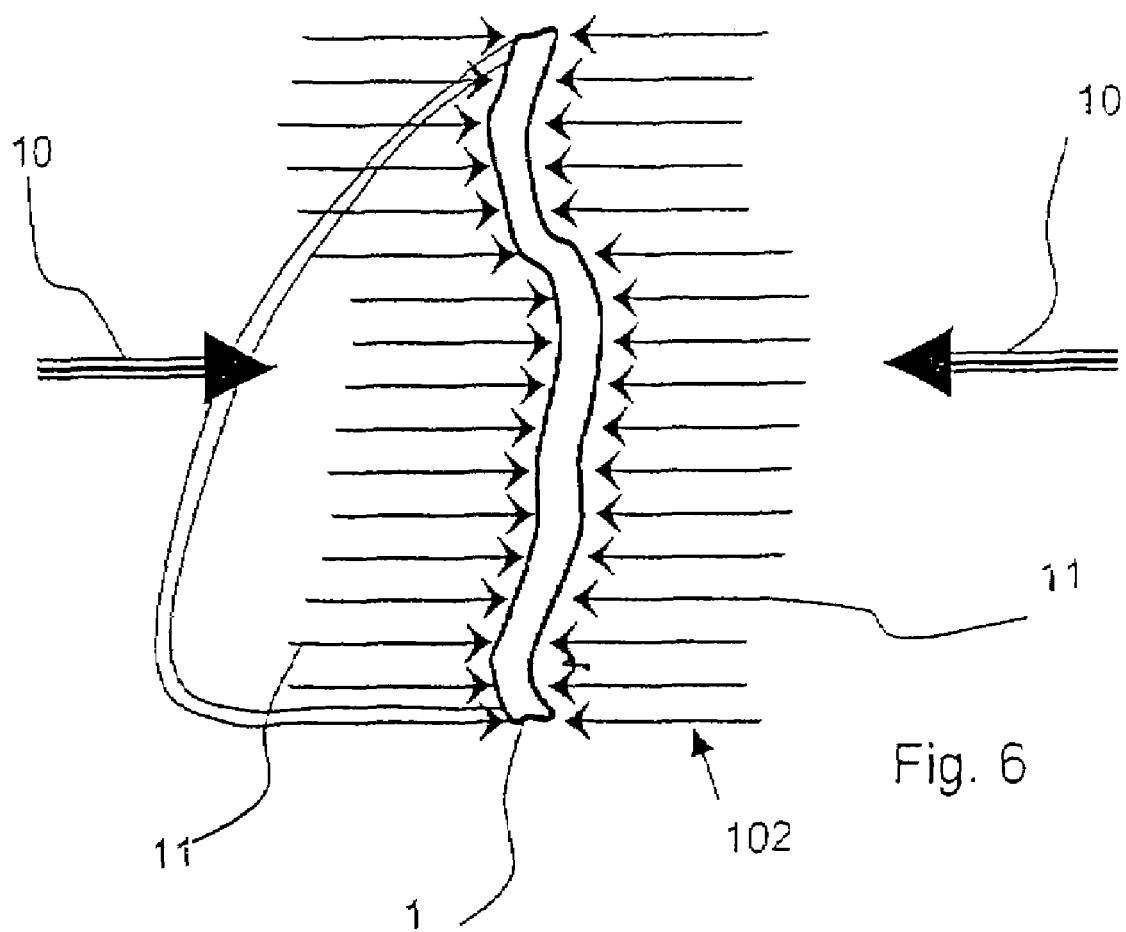
FIG. 6 is a schematic view of an embossing device for the sealing edge.

An embossing device 102 shown schematically in FIG. 6 comprises a plurality of stamps 11, which are arranged opposite each other and receive the sealing frame, FIG. 1. The stamps 11 are arranged uniformly distributed over the circumference of the sealing frame 1 and individual pressing forces 10 are applied to them. A three-dimensional view of the surface of the face is at first generated from the distance data measured with the laser type distance-measuring unit 7 in a control unit, not shown specifically, and actuating signals for the stamps 11 are calculated from these in such a manner that the sealing frame 1 is adapted as a negative mold to the surface of the face.

The deformation of the sealing frame 1 is obtained by the different amounts of displacement of the stamps 11. Stamps 11 located opposite each other now perform displacements by equal amounts in such a way that the distance between the stamps 11 remains unchanged. Stamps 11 located opposite each other now act like tongs, which receive a segment of the sealing frame 1 and displace it into a predetermined position. Another segment of the sealing frame 1 is displaced with adjacent stamps and adapted to the contours of the face. Good adaptation to the contours of the face of the mask user is achieved by the displacement of every individual segment of the circumferential sealing frame.

While specific embodiments of the invention have been shown and described in detail to illustrate the application of the principles of the invention, it will be understood that the invention may be embodied otherwise without departing from such principles.

What is claimed is:

1. A process for adapting a sealing frame of a breathing mask to the shape of a face, the process comprising the steps of:

detecting the contours of the face of the mask user with a distance-measuring device;

making the sealing frame of a plastically deformable material;

providing an embossing device with a plurality of stamps for deforming the sealing frame; and deflecting the stamps on the basis of the distance values determined in the area in which the sealing frame is in contact with the face of the mask user such that the sealing frame corresponds to a negative mold of the contours of the face, wherein:

the breathing mask is formed of a plastic mask body, said plastically deformable sealing frame and a sealing lip;

said plastically deformable sealing frame is formed of a soft plastic material with embedded metal strips;

said sealing lip is formed of plastic material arranged on a side of said sealing frame facing the user of the mask;

said sealing frame is annular and connected to said mask body; and said plastically deformable sealing frame has a plastic material thickness greater than a thickness of said mask body and greater than a thickness of said sealing lip.

2. A process for adapting a sealing frame of a breathing mask to the shape of a face, the process comprising the steps of:

detecting the contours of the face of the mask user with a distance-measuring device;

making the sealing frame of a plastically deformable material;

providing an embossing device with a plurality of stamps for deforming the sealing frame; and deflecting the stamps on the basis of the distance values determined in the area in which the sealing frame is in contact with the face of the mask user such that the sealing frame corresponds to a negative mold of the contours of the face, wherein:

the breathing mask is formed of a plastic mask body, said plastically deformable sealing frame and a sealing lip;

said plastically deformable sealing frame is formed of a plastic material and a reinforcing structure that is at least initially deformable and provides rigidity during use;

said sealing lip is formed of plastic material arranged on a side of said sealing frame facing the user of the mask; and said sealing frame is annular and connected to said mask body.

3. A process in accordance with claim 2, wherein said plastic material of said deformable sealing frame comprises a polyurethane resin; and further comprising:

activating said polyurethane resin with water to cure said polyurethane resin.

4. A process in accordance with claim 3, wherein said reinforcing structure of said deformable sealing frame comprises a polyester fabric as a carrier, which is impregnated with said polyurethane resin.

5. A process for adapting a sealing frame of a breathing mask to the shape of a face of a breathing mask user, the process comprising the steps of:

making the sealing frame of a plastically deformable material with a polyester fabric as a sealing frame carrier, said polyester fabric being impregnated with polyurethane resin, which is water activatable;

providing a mask body of soft plastic material;

providing a sealing lip of plastic material arranged on a user facing side of the sealing frame;

connecting the sealing frame with the mask body of the soft plastic material;

sealing the breathing mask, including the sealing frame together with the mask body and the sealing lip, in an airtight package film;

opening said airtight package film;

removing the breathing mask from the package film;

applying water to the sealing frame after opening said airtight package film; and applying said sealing frame to the face of the breathing mask user after applying said water to said sealing frame such that said sealing frame is molded to a contour of the face of the breathing mask user to cure said sealing frame for maintaining said contour of the face of the breathing mask user after said sealing frame is applied to the face of the breathing mask user.

6. A process in accordance with claim 5, further comprising the steps of:

determining an area in which the sealing frame is in contact with the face of a user such that the sealing frame corresponds to a negative mold of the contours of the face.

7. A process in accordance with claim 6, wherein said step of determining an area includes detecting the contours of the face of the breathing mask user with a distance-measuring device.

8. A process in accordance with claim 7, wherein the contours of the face are scanned line by line.

9. A process in accordance with claim 6, wherein the sealing frame is made to correspond to a negative mold of the contours of the face by:

providing an embossing device with a plurality of stamps for deforming the sealing frame; and deflecting the stamps on the basis of the determined area in which the sealing frame is in contact with the face of the mask user such that the sealing frame corresponds to a negative mold of the contours of the face.

10. A process in accordance with claim 5, wherein activating the sealing frame with an application of water thereto includes wetting said sealing frame with the water.

11. A process in accordance with claim 10, wherein said step of using the breathing mask further comprises placing the sealing frame wet with water on the face of the mask user and adapting the shape of the sealing frame to the shape of the face of the mask user.

12. A process in accordance with claim 10, further comprising curing the sealing frame that has been wetted with water by allowing moisture to escape from a sealing edge of said sealing frame wherein subsequent to adapting the shape of the sealing frame to the shape of the face of the mask user, the breathing mask is maintained in place on the face of the mask user until moisture has escaped.

13. A process in accordance with claim 12, wherein the sealing frame together with the mask body and the sealing lip is sealed in the airtight package film prior to the sealing frame being activated by water.

14. A process in accordance with claim 5, wherein the sealing frame together with the mask body and the sealing lip is sealed in the airtight package film prior to the sealing frame being activated by water.

* * * * *